US010639440B2

(12) United States Patent
Spandorfer

(10) Patent No.: US 10,639,440 B2
(45) Date of Patent: *May 5, 2020

(54) DRUG DISPENSING CONTROLLER AND MONITORING SYSTEM FOR A VENTILATOR

(71) Applicant: iDTx Systems, Inc., Charleston, SC (US)

(72) Inventor: Michael Spandorfer, Charleston, SC (US)

(73) Assignee: iDTx Systems, Inc., Charleston, SC (US)

( * ) Notice: Subject to any disclaimer, the term of this patent is extended or adjusted under 35 U.S.C. 154(b) by 320 days.

This patent is subject to a terminal disclaimer.

(21) Appl. No.: 15/600,362

(22) Filed: May 19, 2017

(65) Prior Publication Data

US 2017/0259017 A1    Sep. 14, 2017

Related U.S. Application Data

(63) Continuation of application No. 14/334,177, filed on Jul. 17, 2014, now Pat. No. 9,675,769, which is a
(Continued)

(51) Int. Cl.
*A61M 16/14*  (2006.01)
*A61M 16/00*  (2006.01)
(Continued)

(52) U.S. Cl.
CPC .... *A61M 16/0003* (2014.02); *A61M 15/0003* (2014.02); *A61M 15/0005* (2014.02);
(Continued)

(58) Field of Classification Search
CPC .. A61M 1/0043; A61M 1/0064; A61M 11/00; A61M 11/005; A61M 11/06;
(Continued)

(56) References Cited

U.S. PATENT DOCUMENTS 4,558,710 A   12/1985 Eichler
4,604,093 A    8/1986 Brown et al.
(Continued)

FOREIGN PATENT DOCUMENTS

GB      2055046      2/1981
WO   WO 98/31413 A1   7/1998

OTHER PUBLICATIONS

Ari et al., A Guide to Aerosol Delivery Devices for Respiratory Therapists, 2$^{nd}$ Edition, American Association for Respiratory Care, © 2009, Exemplary pp. 22, 24 and 34.
(Continued)

*Primary Examiner* — Annette Dixon
(74) *Attorney, Agent, or Firm* — Myers Bigel, P.A.

(57) ABSTRACT

An automated drug delivery and monitoring system for use on mechanically ventilated patients in the intensive care unit is presented. Medication in the form of respirable particles is transported through ventilator circuitry by a delivery unit. Multiple medications may be delivered into the gas flow of the ventilator, with each medication delivered in a defined dose for a frequency and interval as specified by an operator. The particles mixed into the gas flow of the ventilator are inhaled and ingested by the patent's lungs.

**19

Figure 1:
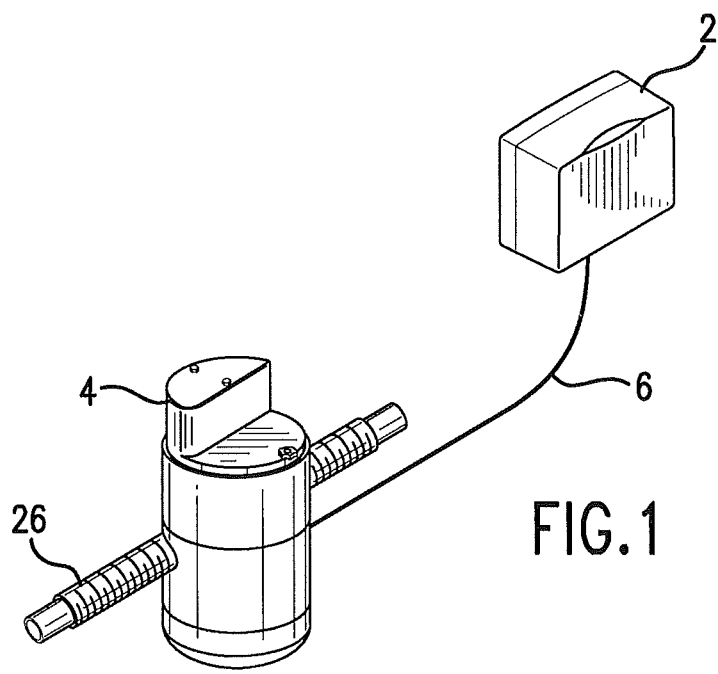
Figure 2:
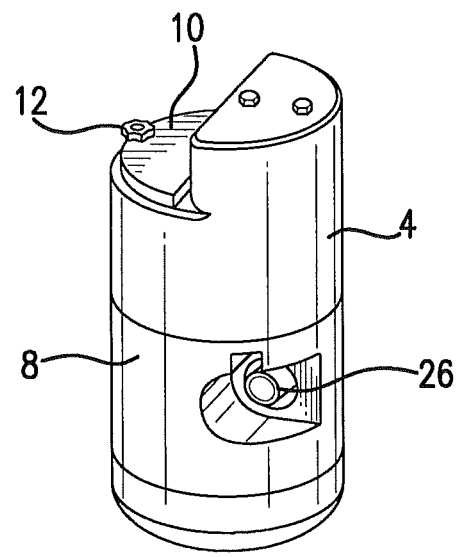
Figure 3:
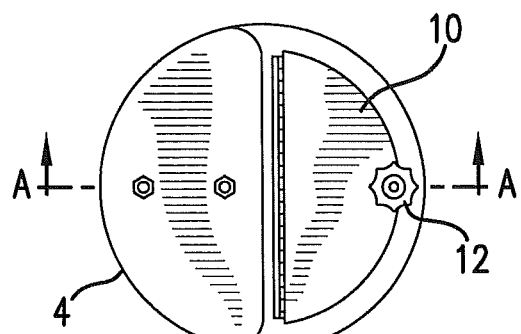

Related U.S. Application Data continuation of application No. 12/138,811, filed on Jun. 13, 2008, now Pat. No. 8,857,429.

(60) Provisional application No. 60/957,486, filed on Aug. 23, 2007, provisional application No. 60/944,326, filed on Jun. 15, 2007.

(51) Int. Cl.
*A61M 15/00* (2006.01)
*A61M 16/08* (2006.01)
*A61B 5/087* (2006.01)
*A61B 5/00* (2006.01)
*A61B 5/085* (2006.01)

(52) U.S. Cl.
CPC ........ *A61M 15/008* (2014.02); *A61M 15/009* (2013.01); *A61M 15/0083* (2014.02); *A61M 16/08* (2013.01); *A61M 16/14* (2013.01); *A61B 5/0075* (2013.01); *A61B 5/085* (2013.01); *A61B 5/087* (2013.01); *A61B 5/4839* (2013.01); *A61M 2016/003* (2013.01); *A61M 2016/0027* (2013.01); *A61M 2016/0036* (2013.01); *A61M 2205/14* (2013.01); *A61M 2205/3368* (2013.01); *A61M 2205/505* (2013.01); *A61M 2205/52* (2013.01); *A61M 2205/8206* (2013.01)

(58) Field of Classification Search
CPC .............. A61M 15/00; A61M 15/0015; A61M 15/0016; A61M 15/0068; A61M 15/0071; A61M 15/0073; A61M 15/0076; A61M 15/0083; A61M 15/0085; A61M 15/0086; A61M 15/009; A61M 16/0051; A61M 16/0057; A61M 16/026; A61M 16/04; A61M 16/0463; A61M 16/0465; A61M 16/0484; A61M 16/06; A61M 16/08; A61M 16/0808; A61M 16/0816; A61M 16/0825; A61M 16/0833; A61M 16/1055; A61M 16/1065; A61M 16/107; A61M 16/1075; A61M 16/14; A61M 16/16; A61M 16/162; A61M 16/209; A61M 2202/0208; A61M 2202/064; A61M 2205/3561; A61M 2205/3569; A61M 2205/3592; A61M 2205/50; A61M 2209/08; A61M 25/0111; B05B 1/262; B05B 7/0012; B05B 7/0483; F16K 5/0207; Y10S 128/912; Y10T 137/4891
See application file for complete search history.

(56) References Cited

U.S. PATENT DOCUMENTS

| | | | |
|---|---|---|---|
| 4,819,629 A | 4/1989 | Jonson | |
| 4,934,358 A | 6/1990 | Nilsson et al. | |
| 4,984,158 A | 1/1991 | Hillsman | |
| 5,002,048 A | 3/1991 | Makiej, Jr. | |
| 5,020,527 A | 6/1991 | Dessertine | |
| 5,103,814 A | 4/1992 | Maher | |
| 5,178,138 A | 1/1993 | Walstrom et al. | |
| 5,186,166 A * | 2/1993 | Riggs .................... | A61M 15/00 128/203.15 |
| 5,277,175 A | 1/1994 | Riggs et al. | |
| 5,284,133 A | 2/1994 | Burns et al. | |
| 5,297,543 A | 3/1994 | Larson et al. | |
| 5,357,946 A * | 10/1994 | Kee .................... | A61M 1/0064 128/200.23 |
| 5,363,842 A | 11/1994 | Mishelevich et al. | |
| 5,392,768 A | 2/1995 | Johansson et al. | |
| 5,394,866 A | 3/1995 | Ritson et al. | |
| 5,404,871 A | 4/1995 | Goodman et al. | |
| 5,431,154 A | 7/1995 | Seigel et al. | |
| 5,437,267 A | 8/1995 | Weinstein et al. | |
| 5,438,982 A | 8/1995 | MacIntyre | |
| 5,474,058 A | 12/1995 | Lix | |
| 5,497,764 A | 3/1996 | Ritson et al. | |
| 5,507,277 A | 4/1996 | Rubsamen et al. | |
| 5,520,166 A | 5/1996 | Ritson et al. | |
| 5,522,378 A | 6/1996 | Ritson et al. | |
| 5,522,385 A | 6/1996 | Lloyd et al. | |
| 5,542,410 A | 8/1996 | Goodman et al. | |
| 5,544,647 A | 8/1996 | Jewett et al. | |
| 5,560,353 A | 10/1996 | Willemot et al. | |
| 5,564,414 A | 10/1996 | Walker et al. | |
| 5,608,647 A | 3/1997 | Rubsamen et al. | |
| 5,617,844 A | 4/1997 | King | |
| 5,622,162 A | 4/1997 | Johansson et al. | |
| 5,622,163 A | 4/1997 | Jewett et al. | |
| 5,655,516 A | 8/1997 | Goodman et al. | |
| 5,676,129 A | 10/1997 | Rocci, Jr. et al. | |
| 5,694,919 A | 12/1997 | Rubsamen et al. | |
| 5,724,957 A | 3/1998 | Rubsamen et al. | |
| 5,738,087 A | 4/1998 | King | |
| 5,743,252 A | 4/1998 | Rubsamen et al. | |
| 5,755,218 A | 5/1998 | Johansson et al. | |
| 5,770,585 A | 6/1998 | Kaufman et al. | |
| 5,794,612 A | 8/1998 | Wachter et al. | |
| 5,809,997 A | 9/1998 | Wolf | |
| 5,826,570 A | 10/1998 | Goodman et al. | |
| 5,881,716 A | 3/1999 | Wirch et al. | |
| 5,967,141 A | 10/1999 | Heinonen | |
| 6,012,450 A | 1/2000 | Rubsamen | |
| 6,014,972 A | 1/2000 | Sladek | |
| 6,079,413 A | 6/2000 | Baran | |
| 6,116,234 A | 9/2000 | Genova et al. | |
| 6,119,684 A | 9/2000 | Nöhl et al. | |
| 6,123,068 A | 9/2000 | Lloyd et al. | |
| 6,138,669 A | 10/2000 | Rocci, Jr. et al. | |
| 6,148,815 A | 11/2000 | Wolf | |
| 6,202,642 B1 | 3/2001 | McKinnon et al. | |
| 6,223,744 B1 | 5/2001 | Garon | |
| 6,237,597 B1 | 5/2001 | Kovac | |
| 6,260,549 B1 | 7/2001 | Sosiak | |
| 6,318,361 B1 | 11/2001 | Sosiak | |
| 6,325,062 B1 | 12/2001 | Sosiak | |
| 6,349,724 B1 | 2/2002 | Burton et al. | |
| 6,358,058 B1 | 3/2002 | Strupat et al. | |
| 6,390,088 B1 | 5/2002 | Nöhl et al. | |
| 6,435,175 B1 | 8/2002 | Stenzler | |
| 6,523,536 B2 | 2/2003 | Fugelsang et al. | |
| 6,529,446 B1 | 3/2003 | de la Huerga | |
| 6,557,552 B1 | 5/2003 | Cox et al. | |
| 6,595,389 B2 | 7/2003 | Fuchs | |
| 6,598,602 B1 | 7/2003 | Sjoholm | |
| 6,615,825 B2 | 9/2003 | Stenzler | |
| 6,631,716 B1 | 10/2003 | Robinson et al. | |
| 6,651,844 B2 | 11/2003 | Tomaka et al. | |
| 6,681,767 B1 | 1/2004 | Patton et al. | |
| 6,684,880 B2 | 2/2004 | Trueba | |
| 6,725,859 B1 | 4/2004 | Rothenberg et al. | |
| 6,830,046 B2 | 12/2004 | Blakley et al. | |
| 6,871,645 B2 | 3/2005 | Wartman et al. | |
| 6,962,152 B1 | 11/2005 | Sladek | |
| 7,185,648 B1 | 3/2007 | Rand | |
| 7,191,777 B2 | 3/2007 | Band et al. | |
| 7,198,044 B2 | 4/2007 | Trueba | |
| 7,201,166 B2 | 4/2007 | Blaise et al. | |
| 7,201,167 B2 | 4/2007 | Fink et al. | |
| 7,347,200 B2 | 3/2008 | Jones et al. | |
| 7,495,546 B2 | 2/2009 | Lintell | |
| 7,549,421 B2 | 6/2009 | Levi et al. | |
| 7,600,511 B2 | 10/2009 | Power et al. | |
| 7,634,995 B2 | 12/2009 | Grychowski et al. | |
| 7,748,382 B2 | 7/2010 | Denyer et al. | |
| 7,905,230 B2 | 3/2011 | Schuler et al. | |
| 8,151,794 B2 | 4/2012 | Meyer et al. | |
| 8,857,429 B2 | 10/2014 | Spandorfer | |
| 9,084,864 B1 * | 7/2015 | Schroeder ......... | A61M 16/0816 |
| 9,675,769 B2 * | 6/2017 | Spandorfer ......... | A61M 15/009 |

(56) References Cited

U.S. PATENT DOCUMENTS

| | | |
|---|---|---|
| 2002/0069869 A1 | 6/2002 | Farmer |
| 2002/0069870 A1* | 6/2002 | Farmer .............. A61M 15/0086 |
| | | 128/200.22 |
| 2003/0200964 A1 | 10/2003 | Blakley et al. |
| 2004/0011358 A1* | 1/2004 | Smaldone .............. A61M 15/00 |
| | | 128/200.24 |
| 2004/0069301 A1 | 4/2004 | Bacon |
| 2004/0084050 A1 | 5/2004 | Baran |
| 2004/0107961 A1 | 6/2004 | Trueba |
| 2004/0138577 A1 | 7/2004 | Kline |
| 2004/0255936 A1 | 12/2004 | Urbanus |
| 2005/0039746 A1 | 2/2005 | Grychowski et al. |
| 2005/0139211 A1 | 6/2005 | Alson et al. |
| 2005/0183725 A1 | 8/2005 | Gumaste et al. |
| 2005/0211245 A1* | 9/2005 | Smaldone .............. A61M 11/06 |
| | | 128/204.18 |
| 2005/0235987 A1 | 10/2005 | Smaldone et al. |
| 2005/0268908 A1 | 12/2005 | Bonney et al. |
| 2005/0274378 A1 | 12/2005 | Bonney et al. |
| 2006/0021614 A1 | 2/2006 | Wermeling et al. |
| 2006/0254581 A1 | 11/2006 | Genova et al. |
| 2007/0151560 A1 | 7/2007 | Price et al. |
| 2007/0157931 A1* | 7/2007 | Parker .................. A61M 11/005 |
| | | 128/204.23 |
| 2007/0173731 A1 | 7/2007 | Meka et al. |
| 2008/0009761 A1 | 1/2008 | Acker et al. |
| 2009/0120431 A1 | 5/2009 | Borgschulte et al. |
| 2009/0137920 A1 | 5/2009 | Colman et al. |
| 2010/0139653 A1* | 6/2010 | Schloss .............. A61M 16/0816 |
| | | 128/203.12 |
| 2013/0081617 A1* | 4/2013 | Cavendish ........ A61M 16/0816 |
| | | 128/203.12 |

OTHER PUBLICATIONS

Carrillo et al., The Development of an Automatic Metered Dose Inhaler, Vanderbilt University Department of BioMedical Engineering, 32 pages, Apr. 27, 2004.

Carrillo et al., Automated Metered Dose Inhaler Presentation #5, Vanderbilt University Department of Engineering, 11 pages, dated Apr. 7, 2004.

European Patent Office communication of a Decision to Grant a European Patent pursuant to Article 97(1) EPC corresponding to European Patent Application No. 08770987.9 (2 pages) (dated Nov. 17, 2016).

Extended European Search Report corresponding to European Patent Application No. 08770987.9 (10 pages) (dated Feb. 28, 2014).

International Search Report and Written Opinion for corresponding PCT Application No. PCT/US2008/066883, dated Oct. 1, 2008.

Ohmeda Project: Automated Metered-Dose Inhaler Deliver Device, Biomedical Engineering Design Projects, College of Engineering University of Wisconsin-Madison, printed from http://homepages.cae.wisc.edu/, printed Jul. 3, 2008, 4 pages, final poster presentation and demo stated to be date May 10, 2002.

Product Specification and Directions, Metered Dose Inhaler (MDI) Adapter, Instrumentation Industries, Inc., 2 pages, (Date of first publication unknown but for exam purposes only, is to be considered before the priority date of the instant application.).

* cited by examiner

DRUG DISPENSING CONTROLLER AND MONITORING SYSTEM FOR A VENTILATOR

RELATED APPLICATIONS

This application is a continuation of application Ser. No. 14/334,177, filed Jul. 17, 2014, which is a continuation of utility application Ser. No. 12/138,811 filed Jun. 13, 2008, which issued as U.S. Pat. No. 8,857,429 on Oct. 14, 2014, and which claims priority to, and the benefit of, provisional application Ser. No. 60/944,326 filed Jun. 15, 2007, and priority to, and the benefit of, provisional application Ser. No. 60/957,486 filed Aug. 23, 2007, the contents of each document are hereby incorporated by reference as if recited in full herein.

FIELD OF THE INVENTION

This invention relates to ventilators and to drug delivery systems.

BACKGROUND OF THE INVENTION

Mechanical ventilation is a method of mechanically assisting or replacing spontaneous breathing when patients cannot do so. One type of ventilation system employs the use of an endotracheal or tracheostomy tube secured into a patient's upper respiratory tract. Gas is mechanically delivered to the patient via the tube. In many cases, mechanical ventilation is used in acute settings such as an intensive care unit for a short period of time during a serious illness. Currently, the main form of mechanical ventilation is positive pressure ventilation, which works by increasing the pressure in the patient's airway and thus forcing additional air into the lungs. To aid in the treatment of ventilated patients, aerosol medicines are aspirated in situ through an access point in the ventilator system. This process is manual, requiring the medical professional to deliver the aerosols on a regular basis.

Bronchodilator and corticosteroid medications for the treatment of reversible airway obstruction are often delivered via inhalation to the lower respiratory tract in both spontaneously breathing and mechanically ventilated patients. The devices typically used for delivery of aerosols to ventilated patients are small-volume nebulizers and pressurized metered-dose inhalers. Small-volume nebulizers and metered-dose inhalers can effectively deliver aerosols in a ventilator model and aerosol delivery can be significantly improved when a proper technique of administration is followed. To enhance lung deposition of aerosols from metered-dose inhalers, several accessory devices have been developed.

The accessory devices most commonly used to deliver aerosols from metered-dose inhalers into ventilator circuits are inline non-chamber devices and inline holding chambers. The advantage of a holding chamber inserted in the ventilator circuit is that the actuated aerosol cloud is retained within the chamber and hence impaction of the drug within the ventilator circuit is reduced.

Goals of this invention include reducing healthcare costs and improving patient safety by automatically administering medication to mechanically ventilated patients.

SUMMARY OF THE INVENTION

An automated drug delivery and monitoring system for use on mechanically ventilated patients in the intensive care unit is presented. Medication in the form of respirable particles is transported through ventilator circuitry by a delivery unit. Multiple medications may be delivered into the gas flow of the ventilator, with each medication delivered in a defined dose for a frequency and interval as specified by an operator. The particles mixed into the gas flow of the ventilator are inhaled and ingested by the patent's lungs.

The device combines monitoring and automated administration to facilitate control of drug delivery. The dispensed medications are preferred to be government approved and accepted as standard of care.

DESCRIPTION OF THE DRAWINGS

FIG. 1 is a schematic view showing a control unit 2 connected to a delivery unit 4.

FIG. 2 is a perspective view of the delivery unit.

FIG. 3 is a top plan view of the delivery unit.

FIG. 4 is a sectioned view taken essentially along line A-A of FIG. 3.

FIG. 5 is a perspective view isolating an index table of a delivery unit and showing metered dose inhalers in position on the index table.

FIG. 6 illustrates an embodiment of a control unit display.

FIG. 7 is a schematic of an embodiment of the invention.

FIG. 8 is a schematic illustrating control functions of an embodiment of the invention.

DESCRIPTION OF PREFERRED EMBODIMENTS

A preferred embodiment of the invention is an automatic drug delivery device for mechanical ventilator tubing circuitry. Metered dose inhalers may be used to deliver drugs into the mechanical ventilator tubing circuitry. The metered dose inhalers may be aerosols. A control unit, which may incorporate a microprocessor, delivers the drugs or other therapeutic agents at a specified time, frequency, dose, and flow triggered to maintain a monitored and consistent delivery of medicaments into the air stream. The device may provide multiple ports to hold and dispense aerosols, which may be in the form of metered dose inhalers. Indicators on an operator interface panel may display delivery and status information, and provide configuration capability to the operator. Patient identification, date, time, medication type, and dose may be logged by the system and can be used for dosage reporting. "Drug" and "medicine" as used herein can mean a drug, medicine, medicament or therapeutic agent dispensed by the device for patient inhalation as delivered through the ventilator circuit.

In one embodiment a control unit 2 communicates with a delivery unit 4. FIG. 1. These components may be linked via a cable 6 carrying both serial communications and power between them. Power may be provided to the operator interface panel via a medical grade AC to DC power supply. A battery system, such as an uninterruptable power source, allows the device to function during times of AC power interruption. The delivery unit, and the point of medication, is preferred to be positioned relatively near the patient, while the control unit may be positioned further away from the patient, which is facilitated by cable 6. The lower voltage DC current of the preferred control unit allows it to be hand held.

The control unit 2 may contain an operator interface panel. The control unit may comprise a microprocessor. The operator interface panel will typically provide for operator input, and will provide output to the delivery unit 4, and it may provide data output. The control unit may be separated from the delivery unit by a power/control cable 6. This configuration facilitates access to the programming features of the system and reduces the size and weight of the section that needs to be in close proximity to the patient and ventilator tubing.

The delivery unit may directly interface with the sensing and control hardware for delivery of medicaments to the air stream. Operation of the delivery unit is under command and control of the control unit, which may be via a serial communications link. The interface provides a means of manual control, status, and data transfer from the operator interface panel.

The delivery unit may be contained in a housing. The housing 8 protects the delivery unit, and also limits access to the drugs or medicaments contained in the housing. The housing may be designed to be tamper-proof, so that it is accessible by hospital staff, such as by providing a lock 12. The top panel 10 of the housing allows access to the internal mechanism of the delivery unit so that drugs may be replaced or replenished. In one embodiment, drugs or other therapeutic agents are delivered in an aerosol form, and the drugs or agents may be delivered by metered dose inhalers.

Figure 4:
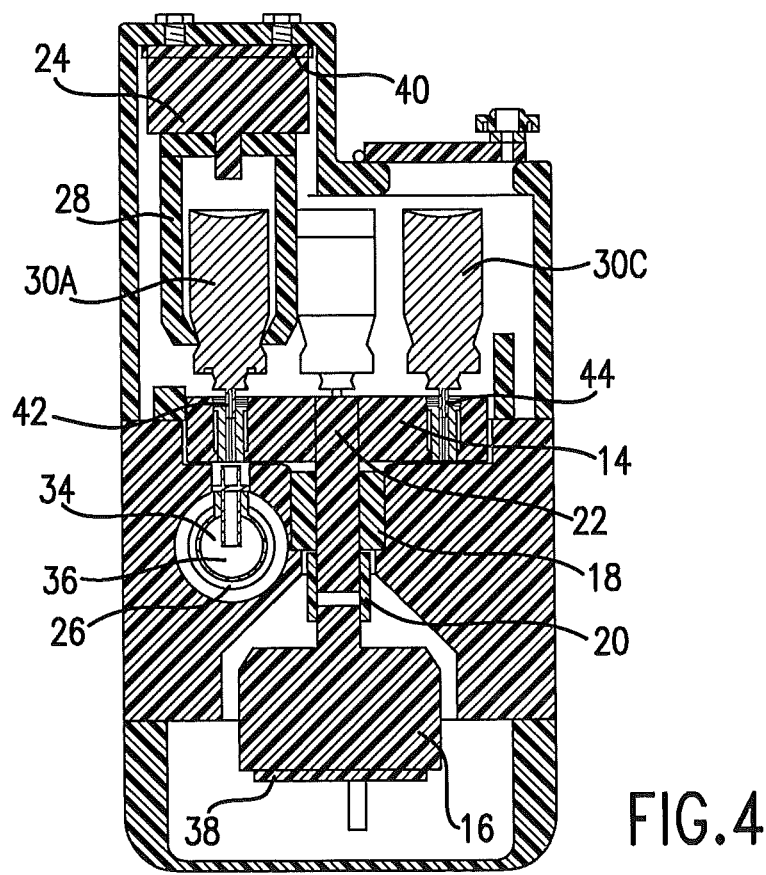

FIG. 4 is a sectioned view of the delivery unit, which is cut away to show internal features of an embodiment of the delivery unit. This embodiment of the delivery unit includes a rotatable index table 14. A rotation device 16 is used to rotate the index table as controlled by the control unit. The rotation device could be a motor, such as a stepper motor, or a rotary solenoid. This rotation device communicates with the index table to rotate the index table by a shaft that rides in a support bearing 18. A coupling 20 may be used to couple the shaft 22 to the rotation device.

An agitator or shaker may be integrated into the index table. Many medications must be agitated before delivery. The control unit causes the agitator to agitate the medication just prior to delivery according to the selected interval for delivery of the particular medication.

Linear actuator 24 may be disposed above a metered dose inhaler 30A that is rotated into position by the index table. The metered dose inhalers exemplified by 30A, 30C are selectively rotated by the index table, as controlled by the control unit, to be in position above the conduit 26 of the mechanical ventilator tubing circuitry. The linear actuator, which may be a linear solenoid, is connected to an actuator, such as actuation jaws 28. In the embodiment shown, the solenoid, acting through the actuation jaws, applies a downward force to the metered dose inhaler 30A. A valve 42 of the metered dose inhaler is opened and dispenses a metered dose into the conduit of the mechanical ventilator tubing circuitry. The control unit times actuation so that the drug or agent is dispensed while the flow of gas through the conduit is toward the patient; that is, while the patient inhales.

The linear actuator may have a position sensor 40 that verifies the position of the linear actuator. This sensor verifies movement of the linear actuator to deliver a dose, and verifies return of the linear actuator after actuation. Return of the linear actuator and the actuation jaws is critical to positioning of the index table for receiving the required metered dose inhaler.

The delivery unit communicates with a conduit 26 that is part of the mechanical Ventilator tubing circuitry. The conduit communicates with the index table as shown.

Figure 5:
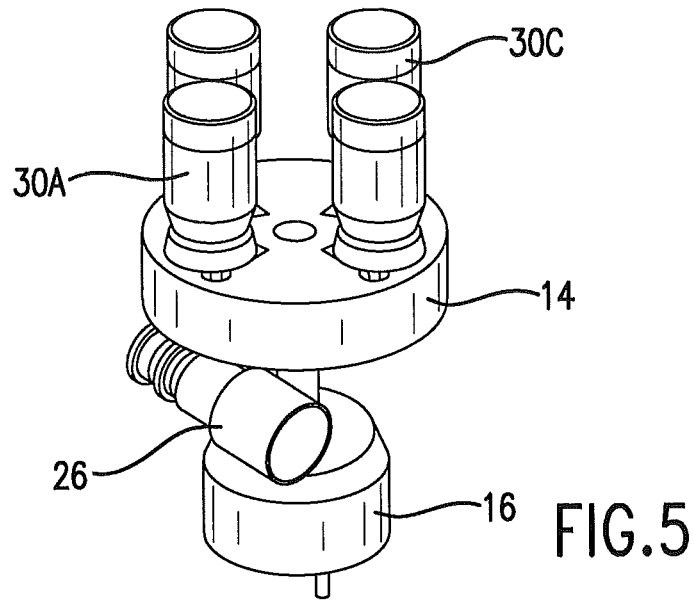

A plurality of metered dose inhalers is present in the delivery unit. As is shown in FIG. 5, in one embodiment of the invention, four (4) metered dose inhalers engage the index table. Fewer than four metered dose inhalers may be used with the device as shown in the drawings. The device could be designed for more than four metered dose inhalers.

As shown in FIG. 4, a non-metal, non-allergic deformable insert 32 is present within the index table. The insert may be formed of plastic, synthetic rubber or similar deformable materials. Not all metered dose inhalers are of identical dimensions at the valve. The insert is deformable, and allows metered dose inhalers and other similar dispensers of various sizes and configurations to be used with the device. Rubber inserts configured for a particular dispenser may be used with the index table.

In another embodiment, a manifold is used rather than the index table. The manifold may receive a plurality of metered dose inhalers, such as four (4) metered dose inhalers. In this embodiment, the manifold has four inlets, and a single outlet, with the single outlet communicating with the conduit of the mechanical ventilator tubing circuitry. In another embodiment, the device could have an equal number of inlets and outlets.

In one embodiment, four linear actuators, each with associated actuation jaws, may be used to selectively actuate the metered dose inhalers. The number of linear actuators will correspond to the number of inlets in the manifold for drug dispensing. The manifold may arrange the metered dose inhalers in an "in line" configuration, or other geometric configurations such as "V" and radial arrangements. The advantage of the index table over the manifold is believed to be that the metered dose inhaler to be actuated may be placed directly above, and in close approximation to, the conduit, leading to an efficient dispensing of the medication as opposed to a manifold, which prevents possible mixing of drugs within a manifold. The use of the insert 32 also allows the device to be cleaned by simply replacing the insert, as opposed to cleaning a manifold into which a plurality of drugs or other materials are dispensed. However, the use of a manifold means that a rotary device is not required, and operation of the device is simplified. The manifold is preferred to have an agitator or shaker for agitating the medication prior to delivery.

The delivery unit may continuously monitor the air pathway flow via a gas flow sensor 34. A flow profile may be established that contains frequency, peak flow, peak flow timing, and duration for both inhalation and exhalation.

Dosage delivery timers are preferred to be maintained for each port. Delivery frequency information may be calculated and configured by the control unit. Dosage counters are preferred to be maintained, with this information conveyed from the delivery unit to the control unit. The dose release sensor 36 may be monitored to detect if the aerosol was delivered into the air stream.

The delivery unit is preferred to have a sensor 44 to determine if an index position presents a drug canister, such as a metered dose inhaler canister. The sensor may be part of the index table.

The delivery unit is preferred to comprise an index sensor 38. The index sensor verifies the position of the index table and the associated drug or agent.

A gas flow sensor 34 is preferred to be used. The gas flow sensor communicates with the conduit. The gas flow sensor measures the direction of flow of gas through the conduit. The gas flow sensor may measure the pressure and/or the rate of change of pressure in the conduit, and may measure other gas flow characteristics such as volumetric gas flow rate and temperature. A primary function of the gas flow sensor is to communicate with the control unit to indicate the direction of flow of gas through the conduit. The release of the drug or agent into the conduit should be timed so that the drug or agent flows with the gas toward the patient. Upon actuation, the air pathway may be monitored by the gas flow sensor to detect the start of the mechanical ventilator gas delivery (inhale). The port may be actuated and the dosage delivered to the conduit at the optimum flow delivery point. The control unit actuates the metered dose inhaler or other device so that drug or agent is released when the flow of gas in the conduit is toward the patient.

The delivery unit signals the control unit to restart the port timer and decrements the dosage counter. The process repeats until commanded to stop or the aerosol cartridge is emptied. Indicators on the delivery unit may indicate actuation, status, alarm and exceptional conditions.

The gas flow sensor, or an additional sensor, may be used to measure pressure and/or the rate of change of pressure in the conduit, and may measure other gas flow characteristics such as volumetric gas flow rate and temperature, that indicate the patient's ability to receive the drug or agent. The gas flow sensor measures circuit conditions and patient airway resistance, which may be used to determine the need for additional medication dosing and timing or modulation of the current specified dosing and timing of the medication. Higher pressure and/or a relatively short cycle time on reversal of gas flow indicate that the ability of the patient to consume the drug or agent through the lungs is impaired. In such case, the control unit may be programmed to increase the dosage frequency to the patient. The programming may occur manually or automatically by an algorithm utilized by the control unit.

The delivery unit may comprise a dose release sensor 36. This sensor verifies that a dose of a drug or agent was actually dispensed and delivered. Verification may be provided and recorded in a data base collection at the control unit or another computer that is in communication with the delivery unit. Similarly, data from other sensors as disclosed herein may be collected and stored in a data base at the control unit or in another computer drive or storage device.

A spectrometer may be disposed in the conduit. The spectrometer measures ultraviolet, optical and near-infrared spectra to determine particle size reflectance and deposition/detection. Raman spectroscopy and optical frequency comb spectroscopy may be incorporated. The spectrometer may be placed at the distal end of the device. The device may also analyze device/ventilator and patient effluent gases.

Figure 7:
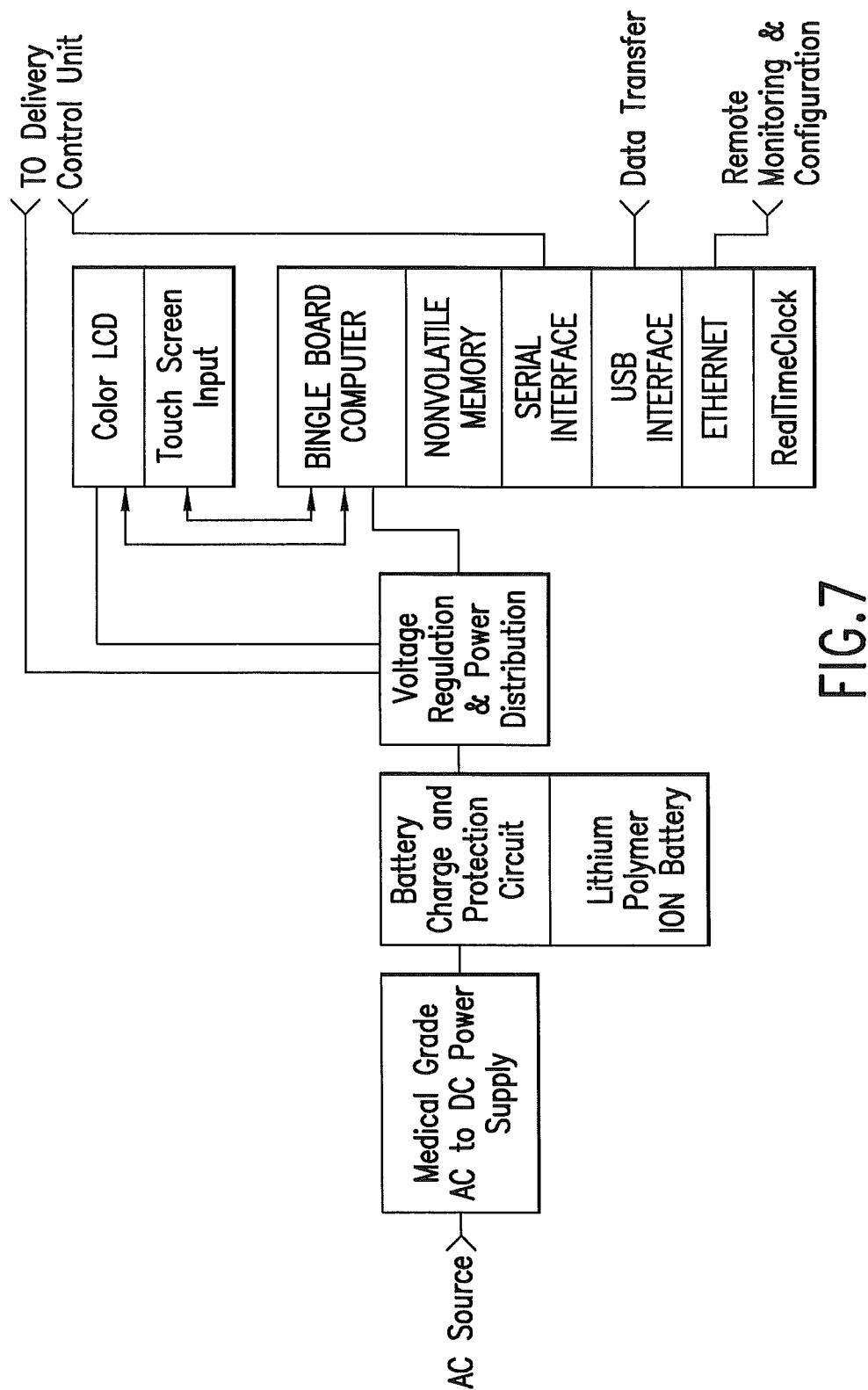
Figure 8:
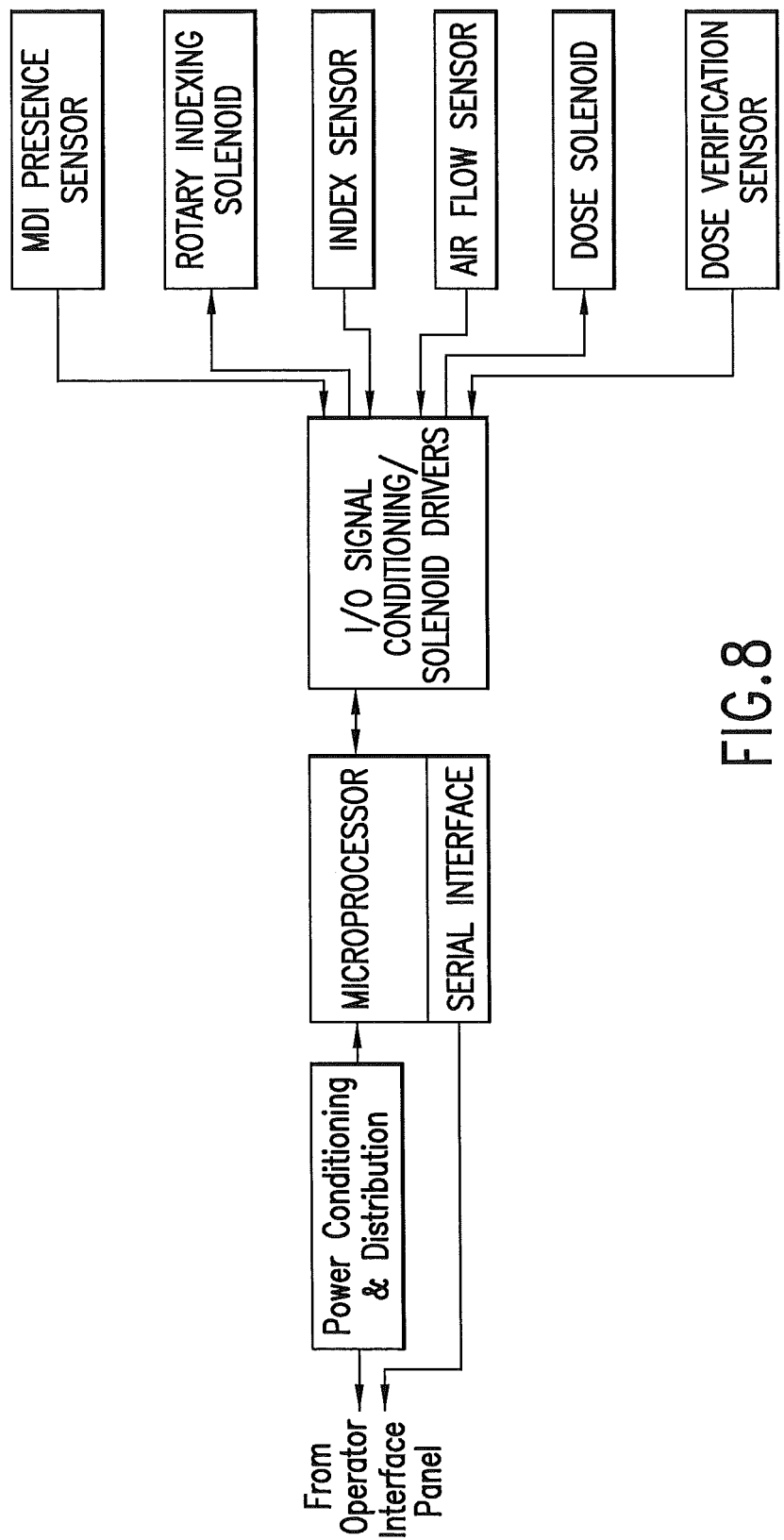

A dedicated industry standard serial communications interface may communicate with the delivery unit. The protocol may be ASCII text based, with sufficient checks to verify message delivery and integrity. A USB interface may provide operator updates of the medications database, and provide patient information and system logs. An Ethernet interface to the control unit may provide remote access from other computer systems for remote monitoring and configuration upload/download. FIG. 7.

Figure 6:
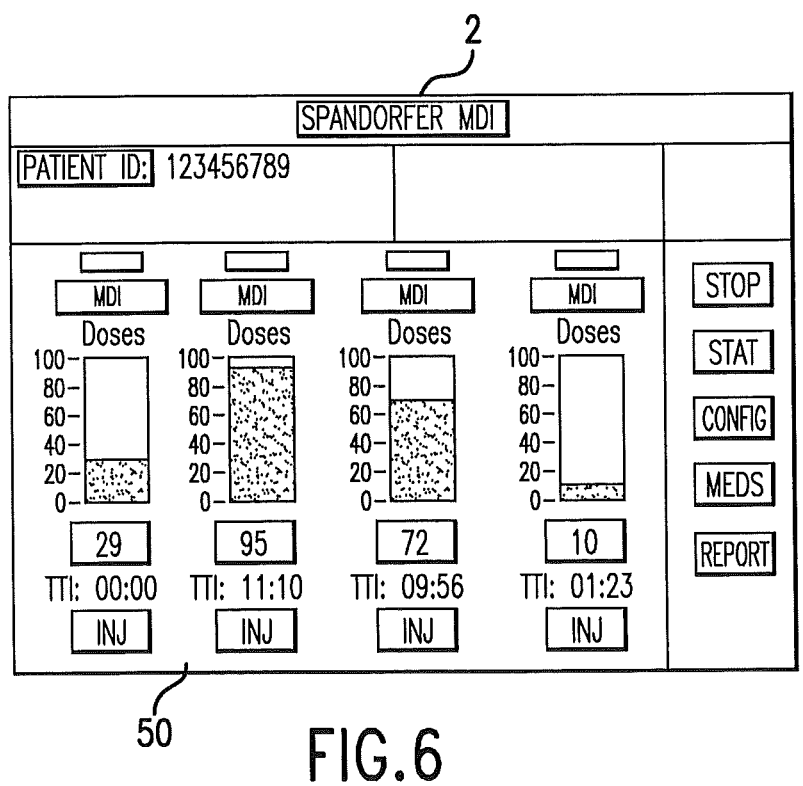

An operator interface panel 50 may comprise a touch screen, flat panel display that will be used to control the delivery unit, and to display system status. FIG. 6. The panel and control unit may allow configuring drug dispensing, such as inputting the desired delivery time and frequency of the plurality of drugs present in the delivery unit. The control unit may maintain logs of usage, medications delivered to the patient, and a drug configuration library.

The operator interface panel may comprise visual data on the screen. A status of each delivery port of the delivery unit is provided. The information may include the number of doses remaining, time to next actuation, frequency of delivery, delivery status, and a manual actuation control.

A menu may display control and configuration selections. A configuration screen may provide controls and methods for configuring the operator interface panel or delivery unit components. The drug database screen will allow monitoring and maintenance of the drug identification, dosage and delivery frequency. The operator may amend entries into the data base. Entries in this database are for use on the main screen when selecting drugs or agents for the delivery port. A reporting screen may display statistics/logs concerning delivery of medications by the system overall and on a per-patient basis. Printing, upload/download will be options provided to the operator. Status/Service screen provides detailed status and diagnostic information about the system. Low level access may be provided through this screen.

The operator interface may comprise a computer with the following components and interfaces: 1) nonvolatile memory for both dosing schedules and dosing data logging; 2) bi-directional serial interface for communicating with the delivery unit. 3) USB interface for data transfer; 4) Ethernet interface for remote monitoring and configuration; 5) touch screen input interface; 6) a color Liquid Crystal Display (LCD) interface; 7) a battery backed real-time clock shall provide a reference for scheduled dosing events; 8) a barcode reader for patient and medication identification, with input into the control unit, hospital databases and/or medication administration records. Output to the operator may be provided by a LCD. Input from the operator may be provided by a touch screen integrated with the LCD.

The invention claimed is:

1. A method for controlling medication dispensed to a ventilator circuit that extends between a mechanical ventilator and a patient, comprising:

providing a housing comprising at least one pressurized metered dose inhaler (pMDI) canister and coupled to a gas conduit having axially opposing and axially extending first and second elongate conduit segments with respective first and second ends, each of the first and second elongate conduit segments being in-line with and adapted to attach to spaced apart segments of tubing of the ventilator circuit to form part of the ventilation circuit;

actuating an actuator in the housing to release medication from the at least one pMDI canister held orthogonal to the gas conduit with a dispensing end of the pMDI canister held proximate the gas conduit in fluid communication with the ventilator circuit via the gas conduit to release medication from the dispensing end to the gas conduit then into the tubing of the ventilator circuit, wherein the actuation of the actuator is timed so that the medication from the at least one pMDI canister is released from the at least one pMDI canister during an inspiratory/inhale cycle with gas flow toward the patient;

monitoring air pathway flow in the ventilator circuit to determine a change in patient airway resistance over time using a controller in communication with at least one sensor coupled to the ventilator circuit, wherein the controller is also in communication with the actuator;

electronically evaluating patient effluent gases in the ventilation circuit;

electronically identifying when a different or additional medication, an increase in dosage and/or a change in scheduled frequency of medication delivered by the at least one pMDI canister is needed based on the determined change in patient airway resistance or the evaluated patient effluent gases or the determined change in patient airway resistance and the evaluated patient effluent gases;

allowing an operator to adjust a defined dosage, delivery time and/or frequency of medication released by the at least one pMDI canister for the actuating; and displaying parameters including number of doses remaining for each of the at least one pMDI canister on a display in communication with the controller.

2. The method of claim 1, wherein the evaluating is carried out using a spectrometer in fluid communication with the gas conduit to obtain one or more of ultraviolet, optical and/or near-infrared spectra, wherein the method further comprises evaluating the obtained spectra to determine particle size reflectance.

3. The method of claim 1, wherein the evaluating is carried out using obtained spectra of the patient effluent gases to determine deposition.

4. The method of claim 1, wherein the controller automatically increases or decreases a dosage frequency or dosage amount or both dosage frequency and amount for the at least one pMDI canister based on the determined change in patient airway resistance.

5. The method of claim 1, wherein the actuator resides above the gas conduit in the housing, and wherein a delivery path from the dispensing end of the at least one pMDI canister is directly into an axially extending flow path that is in-line with the gas conduit and adjacent segments of the spaced apart segments of the tubing of the ventilator circuit.

6. The method of claim 1, wherein the at least one pMDI canister is a plurality of spaced apart pMDI canisters that are held by the housing, and wherein the actuating is carried out in response to the controller directing the at least one actuator to serially actuate the plurality of pMDI canisters to dispense medication into a common entry location into the gas conduit.

7. The method of claim 1, further comprising decrementing a count of a dosage counter in response to actuation of the actuator or a respective pMDI canister and electronically providing a number of doses remaining for the displaying.

8. The method of claim 1, wherein the at least one pMDI canister is a plurality of pMDI canisters held in the housing, wherein the housing is coupled to the ventilator circuit in close proximity to the patient and the tubing of the ventilator circuit.

9. The method of claim 1, further comprising:
determining a cycle time on reversal of gas flow to determine patient airway resistance to assess whether the patient has an impaired ability to intake medication from the at least one pMDI canister through the lungs; and
automatically increasing a dosage frequency or dosage amount or both dosage frequency and amount for the at least one pMDI canister when the controller determines that the patient has the impaired ability.

10. The method of claim 1, further comprising continuously detecting ventilator circuit conditions and patient airway resistance using the at least one sensor, and modifying a next scheduled bolus of medication delivery by adjusting an interval of actuation of the at least one actuator for the at least one pMDI canister in response to determined patient airway resistance using the controller.

11. The method of claim 1, wherein the controller is coupled to an operator interface that comprises a menu with control and configuration selections, and wherein the displaying the parameters is carried out to display, for a respective pMDI canister, a number of doses remaining, time to next actuation, frequency of delivery and delivery status.

12. The method of claim 1, wherein the displaying the parameters is carried out to display a graphic display of a remaining volume or dose amount relative to a full volume capacity and information regarding an interval between dosages for each of the at least one pMDI canister.

13. The method of claim 1, further comprising continuously monitoring the ventilator circuit airflow path during inhalation and exhalation using the controller and the at least one sensor, wherein the in fluid communication with the gas conduit.

14. The method of claim 1, further comprising electronically populating a database of medical records to provide dispensed medication type, dose frequency and verification of medication dispensed to a patient.

15. The method of claim 1, further comprising electronically providing electronic data records of patient physiologic parameters including a flow profile that contains peak flow, peak flow timing, patient airway resistance and duration for inhalation and exhalation using the controller.

16. An automated medical system for controlling medication dispensed to a ventilator circuit that extends between a mechanical ventilator and a patient, comprising:
a gas conduit having axially opposing first and second ends, each end being in-line with and adapted to attach to spaced apart segments of tubing of the ventilator circuit to form part of the ventilation circuit;
a spectrometer in fluid communication with the gas conduit to obtain one or more of ultraviolet, optical and/or near-infrared spectra of patient effluent gas;
a plurality of pressurized metered dose inhaler (pMDI) canisters held orthogonal to the gas conduit with a dispensing end of a respective pMDI canister held proximate the gas conduit in fluid communication with the ventilator circuit via the gas conduit, wherein a delivery path from the dispensing end of the pMDI canisters is directly into an axially extending flow path that is in-line with the gas conduit;
at least one actuator in communication with the pMDI canisters to release medication from the dispensing end to the gas conduit then into the tubing of the ventilator circuit, wherein the at least one actuator can selectively actuate each pMDI canister;
a housing holding the gas conduit, the pMDI canisters and the at least one actuator;
a control unit operably associated with the at least one actuator and comprising an operator interface configured to allow an operator to adjust dosage and schedule medication dispensing for each of the pMDI canisters and to actuate the at least one actuator to dispense medication from each of the pMDI canisters to the ventilator circuit at a defined dosage, delivery time and/or frequency, wherein the control unit monitors air pathway flow in the ventilator circuit and patient effluent gases and is configured to time actuation of the actuator so that medication is released from one or more of the at least one pMDI canisters only during an inspiratory/inhale cycle with gas flow toward the patient, wherein the control unit is further configured to provide electronic data records of patient physiologic parameters including a flow profile; and
a display held by the control unit for displaying parameters including number of doses remaining for each of the pMDI canisters.

17. The system of claim 16, wherein the system evaluates the obtained spectra to determine one or both of (a) particle size reflectance and/or (b) deposition/detection.

18. The system of claim 16, wherein the control unit further determines a pressure and volume of gas flow through the gas conduit associated with patient airway resistance, wherein the control unit determines patient airway resistance and/or a cycle time on reversal of gas flow and evaluates the spectra of the patient effluent gas, and wherein the control unit identifies when additional or different medication, an increase in dosage and/or a change in scheduled frequency of medication delivered by the pMDI canisters is needed based on one or both of the patient airway resistance or the evaluated patient effluent gas.

19. The system of claim 16, wherein the electronic data records of the patient physiologic parameters including the flow profile contains peak flow, peak flow timing, patient airway resistance and duration for inhalation and exhalation,
- wherein the display provides visual information for each of the plurality of pMDI canisters, wherein at least one of the pMDI canisters comprises a different medicine from others of the pMDI canisters,
- wherein the control unit comprises a dosage counter and the visual information comprises information regarding remaining dosages for each of said plurality of pMDI canisters including a graphic display of a remaining volume or dose amount relative to a full volume capacity.

* * * * *

UNITED STATES PATENT AND TRADEMARK OFFICE
CERTIFICATE OF CORRECTION

PATENT NO. : 10,639,440 B2  
APPLICATION NO. : 15/600362  
DATED : May 5, 2020  
INVENTOR(S) : Michael Spandorfer Page 1 of 1

It is certified that error appears in the above-identified patent and that said Letters Patent is hereby corrected as shown below:

In the Claims

Column 8, Line 60, Claim 16:
Please correct "of the at least one pMDI" to read -- of the pMDI --

Column 9, Line 3, Claim 17:
Please correct "deposition/detection." to read --deposition. --

Signed and Sealed this
Eighth Day of September, 2020

Andrei Iancu
*Director of the United States Patent and Trademark Office*